United States Patent
Peters et al.

(10) Patent No.: US 6,293,957 B1
(45) Date of Patent: *Sep. 25, 2001

(54) METHOD OF PERFORMING SINUS SURGERY UTILIZING & SINUS DEBRIDER INSTRUMENT

(75) Inventors: Gary Peters; John T. Cleveland, both of Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/237,404

(22) Filed: Jan. 26, 1999

Related U.S. Application Data

(63) Continuation of application No. 08/752,480, filed on Nov. 19, 1996, now Pat. No. 5,957,881, which is a continuation of application No. 08/422,903, filed on Apr. 17, 1995, now Pat. No. 5,685,838.

(51) Int. Cl.$^7$ .................................................. A61B 17/32
(52) U.S. Cl. ............................................................ 606/167
(58) Field of Search .................................... 606/167, 180, 606/170, 159, 162, 161, 171; 128/898

(56) References Cited

U.S. PATENT DOCUMENTS

| | | |
|---|---|---|
| Re. 33,258 | 7/1990 | Onik et al. . |
| 4,108,182 | 8/1978 | Hartman et al. . |
| 4,167,944 | 9/1979 | Banko . |
| 4,203,444 | 5/1980 | Bonnell et al. . |
| 4,274,414 | 6/1981 | Johnson et al. . |
| 4,705,038 | 11/1987 | Sjostrom et al. . |
| 4,815,462 | 3/1989 | Clark . |
| 4,983,179 | 1/1991 | Sjostrom . |
| 5,059,204 | 10/1991 | Lawson et al. . |
| 5,254,115 * | 10/1993 | Bhatta et al. ......................... 606/170 |
| 5,285,795 | 2/1994 | Ryan et al. . |
| 5,286,253 | 2/1994 | Fucci . |
| 5,322,505 | 6/1994 | Krause et al. . |
| 5,324,301 | 6/1994 | Drucker . |
| 5,490,860 * | 2/1996 | Middle et al. ......................... 606/171 |
| 5,496,314 | 3/1996 | Eggers . |
| 5,685,838 * | 11/1997 | Peters et al. ......................... 606/171 |
| 5,709,698 * | 1/1998 | Adams et al. ......................... 606/180 |
| 5,957,881 * | 9/1999 | Peters et al. ......................... 606/167 |
| 6,042,593 * | 3/2000 | Storz et al. ......................... 606/159 |

* cited by examiner

*Primary Examiner*—Gene Mancene
*Assistant Examiner*—Eduardo C. Robert

(57) ABSTRACT

A method of performing sinus surgery utilizes a sinus debrider instrument having an outer tubular member, an inner member rotatably disposed within the outer member and carrying a tissue cutting surface at a distal end thereof, a suction passage through the instrument for removing cut tissue from a sinus and an annular space between the inner and outer members forming a fluid passage for supplying fluid to the tissue cutting surface. The method includes the steps of positioning the distal end of the instrument at an operative site within the sinus, cutting tissue at the operative site within the sinus by rotating the tissue cutting surface, removing the cut tissue from the sinus through the suction passage and supplying fluid to the tissue cutting surface through the fluid passage to facilitate the removal of cut tissue without introducing fluid to the operative site.

3 Claims, 5 Drawing Sheets

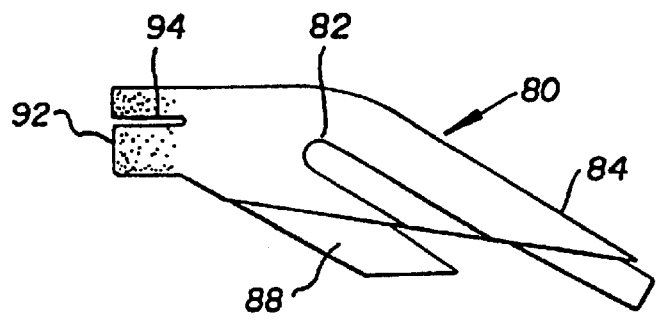
FIG.4
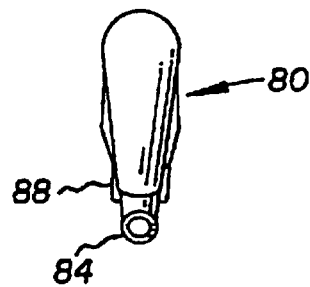
FIG.5
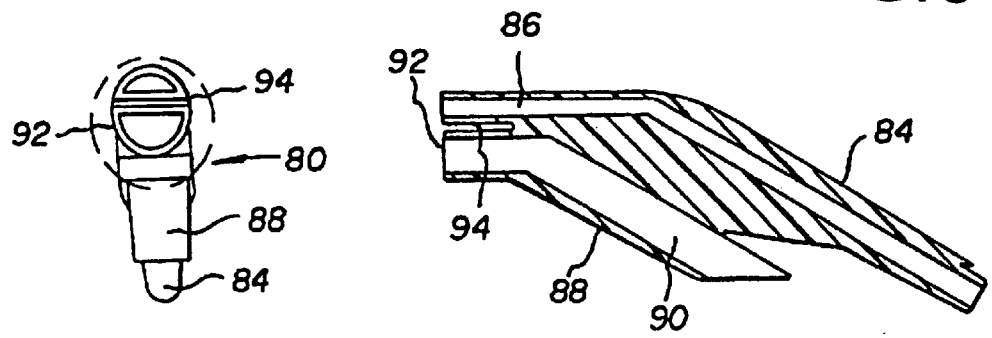
FIG.6
FIG.7
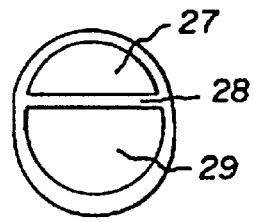
FIG.8
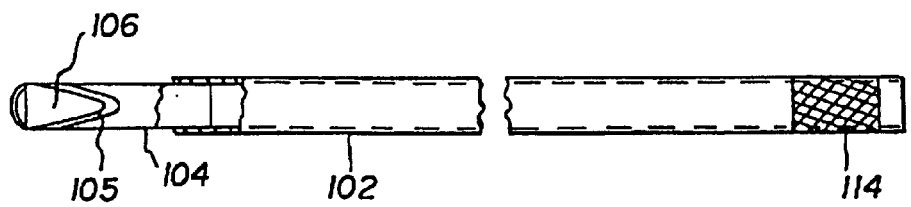
FIG.9

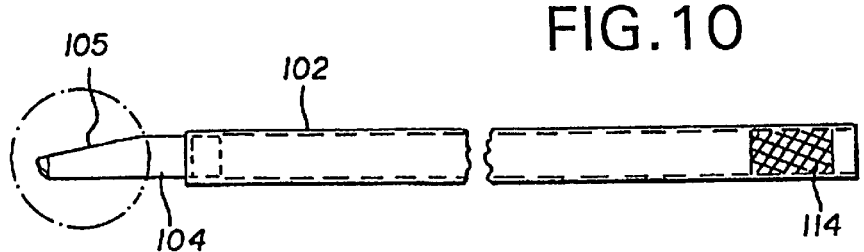
FIG.10
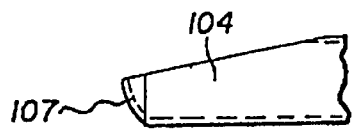
FIG.11
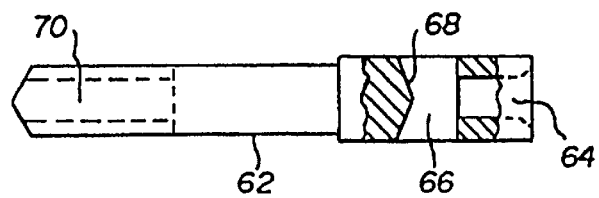
FIG.12
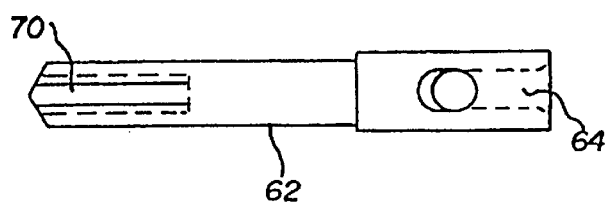
FIG.13
FIG.16 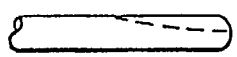    FIG.16A
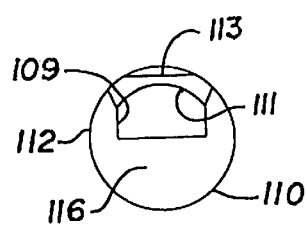   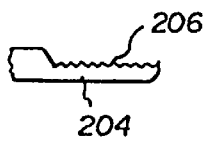 FIG.19
FIG.16B

METHOD OF PERFORMING SINUS SURGERY UTILIZING & SINUS DEBRIDER INSTRUMENT

This application is a continuation of patent application Ser. No. 08/752,480, filed Nov. 19, 1996, now U.S. Pat. No. 5,957,881, which is a continuation of patent application Ser. No. 08/422,903, filed Apr. 17, 1995, now U.S. Pat. No. 5,685,838.

FIELD OF INVENTION

The present invention generally relates to the field of tissue removal and more specifically relates to sinus debriders used for tissue removal during sinus surgery.

BACKGROUND OF THE INVENTION

Generally in the field of sinus surgery, arthroscopic cutting instruments have been used which instruments have encountered numerous problems, the primary one being that the instruments clog or jam from tissue buildup as there is little fluid present at the sinus surgery site unlike the abundance of fluid which occurs in the joints of a human being. Furthermore, when fluid is used with such instruments, it is excessively applied at the surgical site. The tissue jamming or clogging requires frequent cleaning or substitution of the prior art instruments which is not only time consuming thus increasing the time of the procedure as well as decreasing the number of procedures possible in a given operating room facility but also contributes to physician fatigue thus increasing the chances of error.

The following patents constitute representative types of prior art instrumentation directed toward tissue removal.

The prior art is replete with numerous surgical instruments utilizing a cutting tube mounted within an outer cutting housing, the inner cutter member being hollow and connected to a source of suction. These cutting tubes either rotate or reciprocate within the outer tube housing. Examples of such cutting instruments are shown in U.S. Pat. No. 5,324,301, issued on Jun. 28, 1994, and U.S. Pat. No. 5,286,253, issued on Feb. 15, 1994, the latter showing a similar apparatus with a toothed rotating cutter. In such instruments, the cut tissue and other severed material is generally aspirated into a chamber which has a suction removal conduit communicating perpendicularly with the axis of the tubular cutting member or flow of the surgical debris. In U.S. Pat. No. 4,983,179, issued on Jan. 8, 1991, suction is run through the instrument body to a trap in the suction source. Another U.S. Pat. No. 4,274,414, issued on Jun. 23, 1981, discloses an arthroscopic cutter having a coupling member with a central chamber which deflects fluid and tissues cut by the cutter into a cutter tube to a suction box. Another arthroscopic surgery instrument with a blunt cutter tip and similar construction is shown in U.S. Pat. No. 4,203,444, issued on May 20, 1990. A variety of cutter tips which can be used with arthroscopic surgical instruments are shown in U.S. Pat. No. 4,705,038, issued on Nov. 10, 1987, which patent also shows a suction source which extends from the cutter tube through the instrument body exiting out the rear. A cutting lipectomy device which has the suction flowing along a rigid tube parallel to the instrument body is shown in U.S. Pat. No. 4,815,462 issued on Mar. 28, 1989.

U.S. Pat. No. 5,403,276 issued Apr. 4, 1995 is directed toward a combined tissue removal system which uses a reciprocating cutting blade and feedback control for aspiration and irrigation circuits used in the system. Aspiration and suction is varied to the cutting instrument through a foot pedal which is controlled by the operator to set and maintain via valving and transducers the aspiration vacuum and irrigation pressure of the system.

Attempts to overcome clogging and jamming of these types of instruments due to collection of tissue and other materials which have been severed from the body during cutting while performing the surgical procedure has been to attempt to remove these materials so that they will not have a chance to collect in the instrument or pausing during surgery and breaking down and cleaning the instruments. Unfortunately, the cleaning of these instruments can be difficult and time consuming in a surgical environment. U.S. Pat. No. 4,108,182, issued on Aug. 22, 1978, shows a surgical instrument with a removable cutter head. The cutter head is provided with a single lumen exterior conduit leading either to the suction or the fluid source so that fluid or suction can alternately be provided along the single lumen flexible tube to the hollow cutting tube. U.S. Pat. No. 5,059,204 issued on Oct. 22, 1991 discloses an ocular guillotine cutter placed within a swagged outer needle. The cutting head has two removable parts, an infusion sleeve which is provided with a passage for transmission of fluid to the cutting site; and an aspiration sleeve provided with a passage which provides for suction which sucks material through the reciprocating cutter tube from the surgical site. The aspiration sleeve fits on the handpiece by a bayonet pin and the infusion sleeve fits over a collar of the aspiration sleeve in an interference fit.

The present invention has overcome the problems inherent in the prior art devices by providing a dual passage, removable manifold which can be easily removed, cleaned or replaced and a double lumen flexible tube. The cutter head body into which the manifold is mounted is also easily removed from the apparatus.

The double lumen flexible tube which supplies both the suction and fluid is mounted in a channel cut into the instrument body with the tube terminating at one end of the removable manifold. Thus, separate passageways for suction and fluid are provided in the invention. It should be noted that in arthroscopic surgery, there is normally a great deal of fluid present at the site of the surgery so that fluid is not required, but in sinus surgery which is the primary direction of the present invention, there is little moisture, so moisture must be supplied to keep the tissue material from clogging up the device.

The instrument is also provided with a nipple projection extending into the tube channel so that a surgeon can easily grasp the flexible tube and with slight finger pressure, decrease the amount of suction or the amount of fluid going to the operation site.

SUMMARY OF THE INVENTION

The present invention is directed toward a sinus cutting instrument comprising a housing, a motor mounted in the housing and a cutter head mounted to the housing. The cutter head is frustum conical shaped and defines an interior chamber, a suction passageway and a fluid passageway. A blade holder is mounted to the cutter head and is axially aligned with the interior chamber. A coupling member is mounted in the interior chamber and connects the motor and the blade member to transmit motion from the motor shaft to the blade member which is rotatably mounted in the blade holder. A removable manifold member defining separate passageways communicates with the suction passageway and the fluid passageway of the head and is formed with a connection section to hold a double lumen flexible tube providing suction and fluid to the cutter head and operation site.

It is an objection of the invention to provide a lightweight easily handled surgical instrument which can be readily cleaned and/or sterilized.

It is another object of the invention to provide an instrument which allows the surgeon to manually change the amount of fluid delivered to the surgical site and the amount of suction applied at the surgical site.

It is yet another object of the invention to provide a central suction chamber in the instrument which deflects tissue and cut materials directly into the suction line for later filtration of the material.

In the accompanying drawings, there is shown an illustrative embodiment of the invention from which these and other of objectives, novel features and advantages will be readily apparent.

BRIEF DESCRIPTION OF THE DRAWINGS

FIG. 4 is an enlarged side elevational view of the fluid manifold of the debrider apparatus;

FIG. 5 is a front elevational view of the fluid manifold shown in FIG. 4;

FIG. 6 is a rear elevational view of the manifold shown in FIG. 4;

FIG. 7 is a cross sectional view of the fluid manifold shown in FIG. 4;

FIG. 8 is an enlarged cross sectional view of the flexible tube;

FIG. 9 is a top plan view of the outer cutter tube holder;

FIG. 10 is a side elevational view of the cutter tube holder shown in FIG. 9;

FIG. 11 is an enlarged side elevational view of the end of the cutter tube holder shown in FIG. 10;

Figure 12 is an enlarged side elevational view partially in section of the drive coupler member;

FIG. 13 is a top plan view partially in phantom of the drive coupler member shown in FIG. 12;

FIG. 16 is an enlarged view of the cutter tube tip shown in FIG. 15;

FIG. 16(a) is a front elevational view of the cutter tube tip shown in FIG. 16;

FIG. 16(b) is an enlarged front elevational view of the cutter tube tip shown in FIG. 16;

FIG. 19 is an enlarged side elevational view of the cutter tip of the cutter tube shown in FIG. 18.

DETAILED DESCRIPTION OF THE INVENTION

Figure 1:
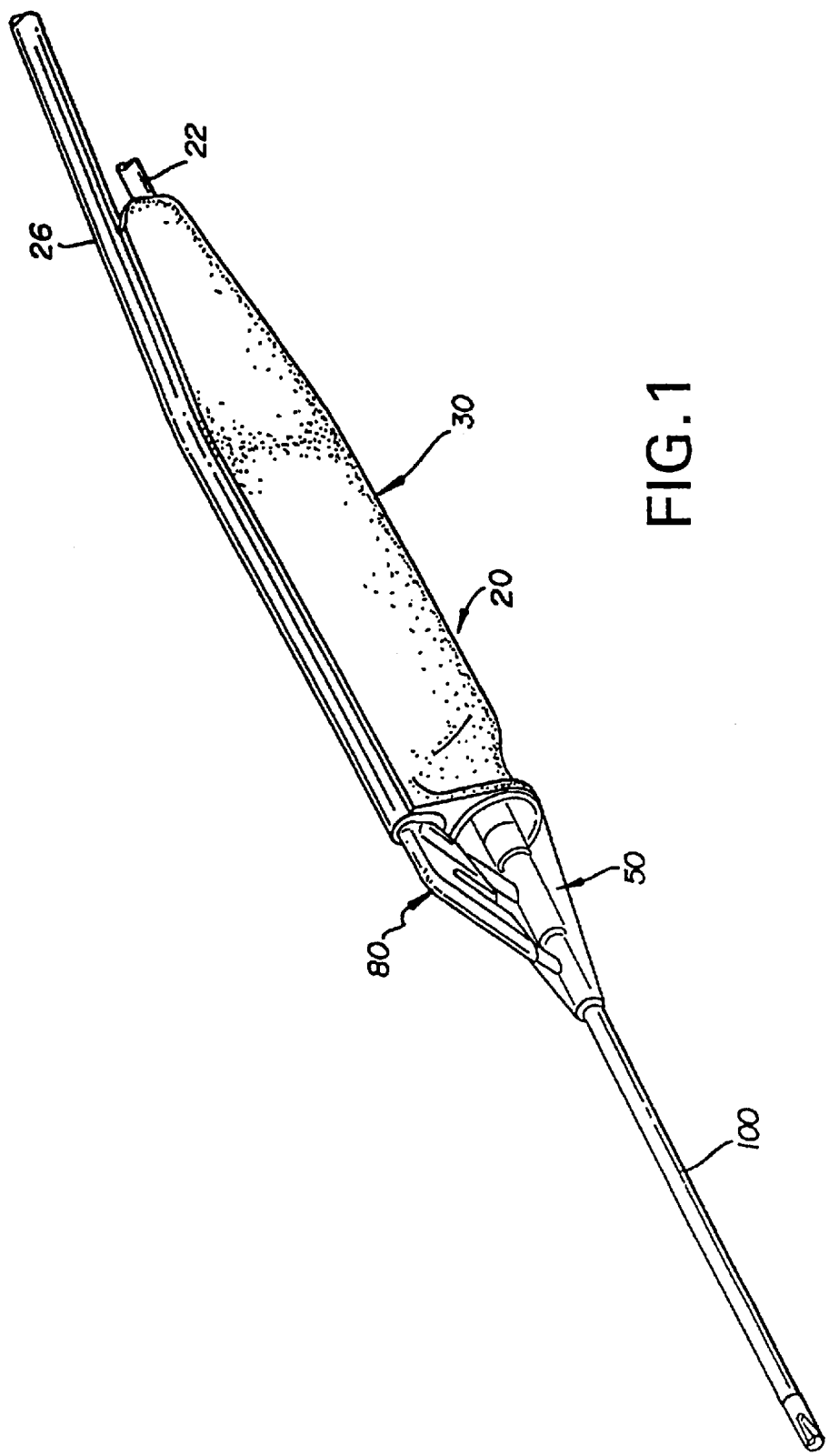
FIG. 1 is a perspective view of the debrider apparatus.
Figure 2:
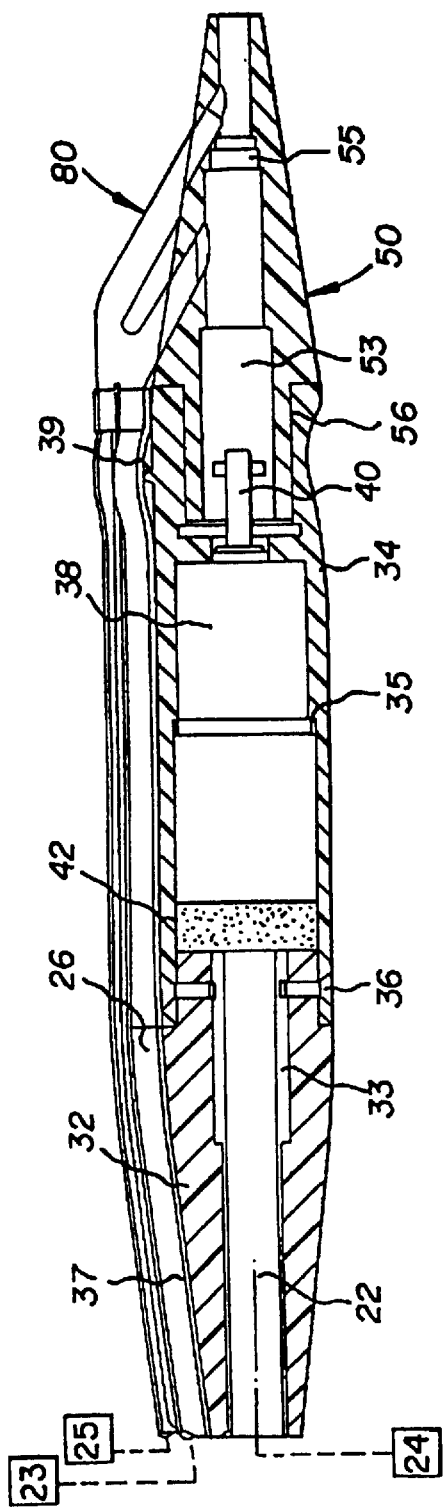
FIG. 2 is a cross section of the debrider apparatus shown in FIG. 1 without its cutter assembly.
Figure 3:
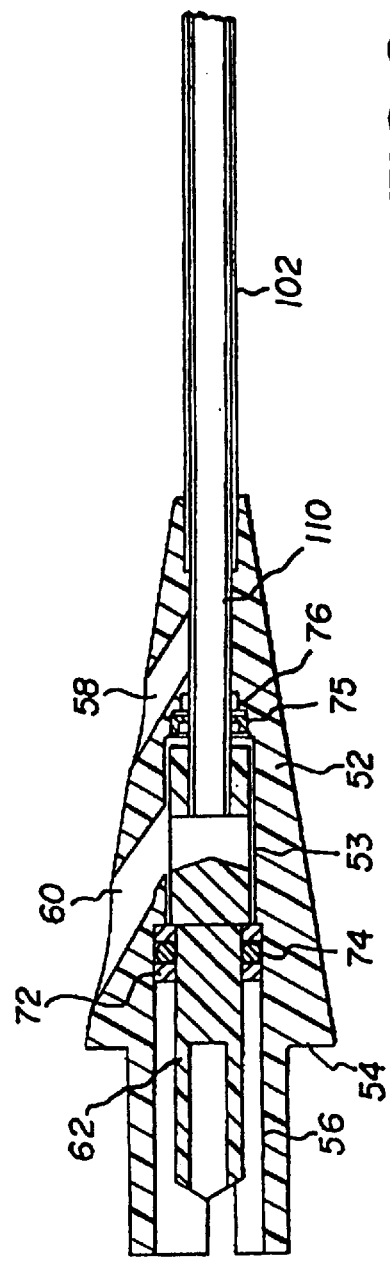
FIG. 3 is a cross section of the cutter head assembly with cutter assembly.
Figure 14:
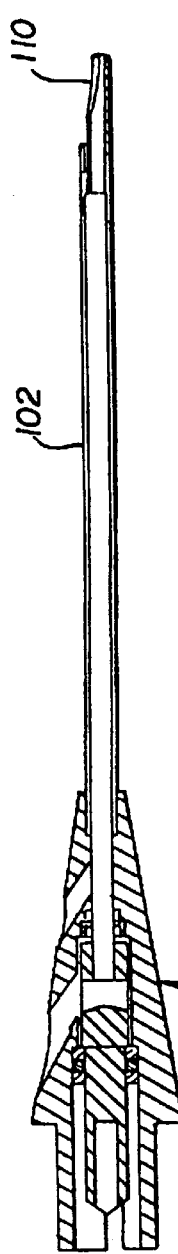
FIG. 14 is a cross section view of the cutter head assembly with cutter assembly.

The preferred embodiment and best mode of the invention is shown in FIGS. 1 through 19.

In the inventive sinus debrider apparatus 20, the instrument is constructed with a body 30, a cutting head assembly 50 mounted in the body 30 and a manifold 80 mounted in the cutting head assembly.

The body 30 which serves as the handle of the instrument is preferably in two sections formed with a motor housing cap 32 and a hand piece 34 which are mounted together and secured by screws 36. The hand piece 34 defines a stepped cavity 35 which contains a motor 38 and a power and signal cord 22 connected to the motor. The cord 22 extends out the back of the hand piece. The motor 38 has a drive shaft 40 which extends into an axially aligned end cavity which the cutter head assembly is seated in and a corresponding stepped coupler cavity or chamber 53 formed in the cutter head assembly 50. The drive motor 38 is adapted to rotate the blade member, or cutter or cutting tube, 110 at shearing speeds in a clockwise, counter clockwise or oscillation rotation in response to signals from an outside control foot pedal so that the tissue material is cut into discrete pieces. The rear of the motor engages silicone buffer member 42 to hold the motor in place in the cavity 35 and also to damper motor vibrations. A power source and motor control source is shown by block diagram 24 and this source is connected by a power cord 22 to the motor 38 to provide both power and signals for operating the motor in forward, reverse and oscillating manner. The power cord 22 runs through a smaller diameter section of a stepped chamber 33 cut in the motor housing cap. The hand piece 34 and motor housing cap 32 which form body 30 are provided with a groove 37 on the outer surface. The groove 37 has rounded side walls and an opening into the atmosphere which is smaller in width than the width of the flexible tube so that the flexible tube which has a diameter greater than the opening width may be forced down into the groove and held in place by the inner walls of the groove. A nipple 39 extends outward from the hand piece 34 into the groove 37 and engages the flexible fluid supply tube 26. This nipple allows the surgeon to press down on the flexible double lumen tube 26 to reduce suction to the operation site. The groove 37 holds and retains the double lumen fluid transmission tube 26 which is in turn fastened to the fluid conduit connector end 92 of manifold 80 and at its distal end to a suction source such as a vacuum generator 23 and a fluid supply source 25 as shown in block diagram. The use of outside fluid and suction sources is well known in the art. The tube functional cross section as best represented in FIG. 8 has a liquid lumen 27 which is divided by separating wall 28 from a suction lumen 29.

The cutter head assembly 50 is formed with a frustum conical body 52 defining a shoulder 54 and a rear connector tubular portion 56. The connector portion 56 snugly fits in the end cavity of hand piece 34 in 3-pin bayonet fit with shoulder 54 abutting the planar end surface of the hand piece. The body 52 defines a fluid channel 58 and a suction channel 60 which communicate at an angle with a central stepped chamber 53, chamber 53 being formed in axial alignment in the body 52. A drive coupler member 62 is mounted in the stepped chamber 53 and engages motor shaft 40 on one end and cutting tube 110 on the other end so that the torque generated by the motor shaft 40 is transmitted to the cutting tube 110 or 202. The coupler member 62 has a stepped body of A.B.S. approximately 1.6 inches in length and defines an annular cutting tube seat 64 on one end which cutting tube seat leads into and communicates with deflection chamber 66. The cutting tube seat end is chamfered for approximately 0.03 inches at a 45 degree angle to the center axis to aid in receiving the cutting tube. The rear downstream wall 68 of deflection chamber 66 is formed into a bevel which keeps debris from the surgery from collecting and jamming in the instrument. The deflector wall 68 allows easy transmission of the tissue and other material which has been cut and removed back through suction channel 60 into the suction manifold 80. The distal portion of the coupler member which is of a lesser diameter than the cutting tube portion is formed with an annular blind bore 70 which forms the motor shaft seat. The coupler member 62 is thus able to be seated within the coupler section of chamber 53 and easily rotate around within the chamber. Two retainer rings 72 with a viton O-ring 74 placed between the rings are mounted around the rear stepped end of the coupler member and engage the chamber walls of the body 52 defining the stepped coupler chamber 53. A retainer ring 75 and front seal 76 are positioned in the forward stepped seal section 55 of the coupler chamber to preclude fluid from flowing back from fluid channel 58.

The manifold 80 is preferably of one piece clear polycarbonate construction with a body 82 branching into a tubular fluid conduit 84 defining a fluid passage 86 and a suction conduit section 88 defining a suction passage 90. Channels or passages 86 and 90 are angularly orientated within the body 82 forming a 30 degree bend allowing the double lumen tube 26 to be placed parallel to the handle of the instrument. Both fluid passages are separated and form a tube connector end 92 as is clearly shown in FIGS. 4 and 7. The double lumen tube 26 snugly fits over the end 92 with lumen separator wall 28 of the tube fitting into gap 94 formed in the tube connector end 92. Each lumen of the tube is formed with a semicircle configuration with fluid lumen 27 being smaller in cross section than suction lumen 29.

Figure 15:
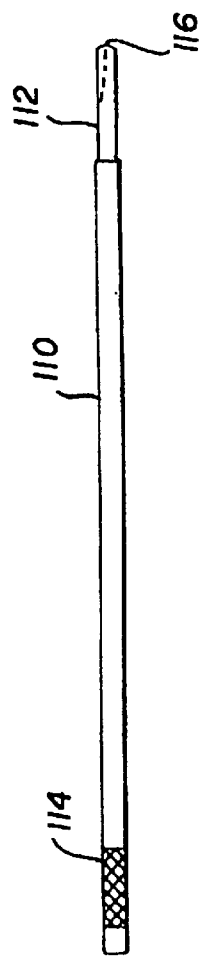
FIG. 15 is an elevational side view of the cutter tube of the cutter assembly shown in FIG. 14.

The cutter assembly 100 is mounted in the proximal end of coupler cavity 57 and is secured in place by an adhesive or other means. The cutter tube holder or outer tube 102 has a polished surface with a knurled distal end portion and carries within it an end piece 104 which is cut with flat edges 105 running from a point past the axis of the tube at approximately an 11 degree angle to form a tissue engagement opening 106 and a spherical end 107. The end piece 104 is secured to tube 102 by brazing, although other means can be used. The end piece runs approximately 0.570 inches in length. The outer tube 102 has an outer diameter of 0.134 inches and an inner diameter of 0.1150 inches. Mounted inside the outer tube 102 is a cutting tube 110 which has a sharpened cutting tip 112 and knurled distal end portion 114. The cutting tube defines a lumen 111 therethrough communicating between a tissue cutting surface 109 at distal cutting tip 112 and deflection chamber 66 adjacent the proximal end of the cutting tube. The cutting; This tube is seen in FIGS. 15, 16, 16(a), 16 (b). The cutting tip 112 is ground flat, as shown at 113 in FIGS. 16(a) and 16(b); 0.007 inches deep and has a closed spherical end 116. The cutting tube 110 has an outer diameter of 0.1149 inches or a diameter which is smaller but of close tolerance with the inner diameter of the outer tube with the end mounted in coupler member being knurled so that it is firmly held in the coupler member.

Figure 17:
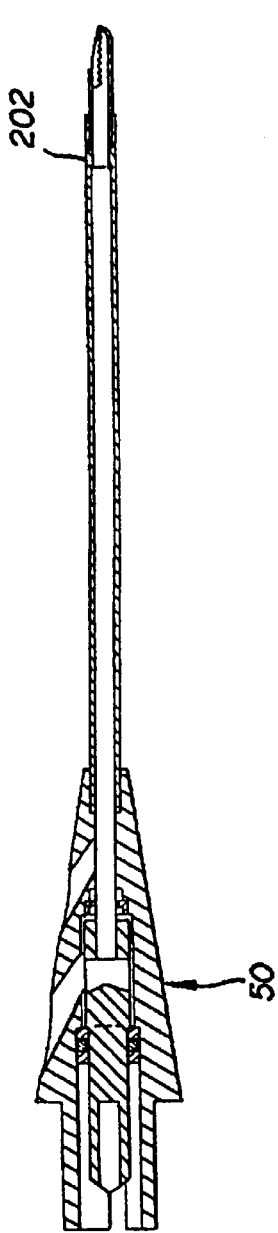
FIG. 17 is a cross section view of a cutter head assembly with an alternate cutter tube embodiment.
Figure 18:
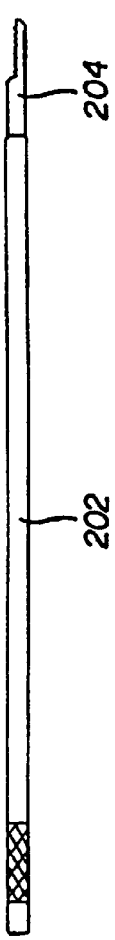
FIG. 18 is a side elevational view of the cutter tube used in FIG. 17.

An alternate embodiment of the invention is shown in FIGS. 17 through 19. In this alternate embodiment, the instrument construction is identical with that previously disclosed with the exception that the cutter tube 202 is provided with a cutting tip 204 having a plurality of teeth 206 with slightly curved sides and rounded bottoms, the crest of the teeth extending above the axis of the cutter tube 202.

In operation, the instrument is positioned to cut tissue with the suction and fluid modes activated. The cutter blade is activated by a foot switch and the surgeon increases or decreases the fluid to the surgical site by depressing the flexible tube so that the top lumen 27 of the double lumen tube is constricted reducing fluid flow. Alternatively, suction is reduced by depressing the flexible tube over nipple 39 to constrict the suction lumen 29 and reduce suction from the site. Thus, fluid or suction can be manually controlled by the surgeon's hand while rotation of the blade in either direction or an oscillating motion is controlled by a foot pedal.

In the foregoing description, the invention has been described with reference to a particular preferred embodiment, although it is to be understood that specific details shown are merely illustrative, and the invention may be carried out in other ways without departing from the true spirit and scope of the following claims.

What is claimed is:

1. A method of performing sinus surgery utilizing a sinus debrider instrument having an outer tubular member with an opening at a distal end thereof, an inner member rotatably disposed within the outer tubular member with a tissue cutting surface of the inner member adjacent the opening in the outer tubular member, and an annular space between the outer tubular member and the inner member forming a fluid passage to deliver fluid to the tissue cutting surface, said method comprising the steps of positioning a distal end of the sinus debrider instrument at an operative site within a sinus;

cutting tissue at the operative site within the sinus with the tissue cutting surface by rotating the inner member relative to the outer tubular member;

removing tissue cut by the tissue cutting surface from the sinus through a suction passage in the sinus debrider instrument; and supplying fluid to the tissue cutting surface through the fluid passage in the sinus debrider instrument to facilitate the removing of cut tissue from the sinus.

2. The method of performing sinus surgery as recited in claim 1 wherein the inner member is tubular and has a lumen therein and wherein said step of removing cut tissue from the sinus includes aspirating the cut tissue through the lumen in the inner member.

3. A method of performing sinus surgery utilizing a sinus debrider instrument having an outer tubular member with an opening at a distal end thereof, an inner member rotatably disposed within the outer tubular member with a tissue cutting surface of the inner member adjacent the opening in the outer tubular member, and an annular space between the outer tubular member and the inner member forming a fluid passage to deliver fluid to the tissue cutting surface, said method comprising the steps of positioning a distal end of the sinus debrider instrument at an operative site within a sinus;

cutting tissue at the operative site within the sinus with the tissue cutting surface by rotating the inner member relative to the outer tubular member;

removing tissue cut by the tissue cutting surface from the sinus through a suction passage in the sinus debrider instrument; and supplying fluid to the tissue cutting surface through the fluid passage in the sinus debrider instrument to facilitate the removing of cut tissue from the sinus, said step of supplying fluid including supplying fluid from the fluid passage directly to the tissue cutting surface.

* * * * *